(12) United States Patent
Granger et al.

(10) Patent No.: US 6,211,201 B1
(45) Date of Patent: Apr. 3, 2001

(54) MULTIVALENT SALTS OF PYRIDOSTIGMINE AND RELATED COMPOUNDS

(75) Inventors: Colin Granger; Robert Orr, both of Costa Mesa; Kandasamy Ramasamy, Laguna Hills, all of CA (US)

(73) Assignee: ICN Pharmaceuticals, Inc., Costa Mesa, CA (US)

( * ) Notice: Subject to any disclaimer, the term of this patent is extended or adjusted under 35 U.S.C. 154(b) by 0 days.

(21) Appl. No.: 09/308,723

(22) PCT Filed: Nov. 10, 1997

(86) PCT No.: PCT/US97/20509

§ 371 Date: Jun. 29, 1999

§ 102(e) Date: Jun. 29, 1999

(87) PCT Pub. No.: WO98/22458

PCT Pub. Date: May 28, 1998

Related U.S. Application Data

(60) Provisional application No. 60/031,186, filed on Nov. 19, 1996.

(51) Int. Cl.[7] .................. A61K 31/444; A61K 31/357; C07C 271/42; C07D 401/06; C07D 407/06
(52) U.S. Cl. .................. 514/335; 514/422; 514/454; 514/467; 514/488; 514/643; 546/261; 548/51; 549/388; 549/448; 560/133; 564/286
(58) Field of Search .................. 546/261; 548/519; 549/388, 448; 560/133; 564/286; 514/335, 422, 454, 467, 488, 643

(56) References Cited

U.S. PATENT DOCUMENTS

| | | | |
|---|---|---|---|
| 4,246,416 | * | 1/1981 | Sommer et al. .................. 546/261 |
| 4,672,120 | * | 6/1987 | Sommer et al. .................. 546/261 |
| 4,677,222 | * | 6/1987 | Sommer et al. .................. 560/133 |
| 4,686,293 | * | 8/1987 | Sommer et al. .................. 546/261 |
| 4,692,530 | * | 9/1987 | Sommer et al. .................. 546/261 |

* cited by examiner

Primary Examiner—Richard L. Raymond
(74) Attorney, Agent, or Firm—Fish & Associates, LLP; Robert D. Fish

(57) ABSTRACT

A quaternary ammonium cholinergic agent is complexed with a multivalent anion, or with multiple monovalent anions. The complex may be administered orally to a patient to treat pain, or for some other purpose. Numerous modifications are contemplated, including modifications to the ring structure of the compound, substitution and functionalization of the ring. Other contemplated modifications include the use of different anions, including various monovalent and polyvalent anions, and both organic and inorganic anions. The compounds have utility as cholinergic agents, and especially in the treatment of mysasthenia gravis, chest pain, and carpal tunnel syndrome.

20 Claims, 3 Drawing Sheets

MULTIVALENT SALTS OF PYRIDOSTIGMINE AND RELATED COMPOUNDS

This application claims the benefit of International Application No. PCT/US97/20509 filed Nov. 10, 1997 which claimed the benefit of U.S. provisional application number 60/031,186 filed Nov. 19, 1996, both incorporated herein by reference in their entirety.

FIELD OF THE INVENTION

The field of the invention is cholinergic agents.

BACKGROUND

Pyridostigmine 3-[[(Dimethylamino)-carbonyl]oxy]-1-methylpyridinium (Mestinon™), and Neostigmine 3-[[(Dimethylamino)-carbonyl]oxy]-N,N,N-trimethylbenzeaminium (synstigmin), and Edrophonium N-Ethyl-3hydroxy-N, N-dimethylbenzenaminium are all cholinergic agents. These compounds have several known uses including treatment of mysasthenia gravis, esophageal chest pain, and pre-exposure antidote to chemical warfare nerve agents. These compounds may also be useful in treating carpel tunnel syndrome.

Pyridostigmine and neostigmine are generally administered to a patient as a bromide salt, while Edrophonium is generally administered as a chloride salt. While these known monovalent salts are generally considered to be adequate, it is now contemplated that multivalent salts would potentially be more stable, and may have better physical characteristics, especially in solid physical dosage form. There may also be advantageous pharmokinetics over the monovalent salts. Still fturther it is contemplated that compounds having multiple quaternary ammonium sites may have usefll pharmaceutical benefits.

SUMMARY OF THE INVENTION

According to the present invention quaternary ammonium cholinergic agents are complexed with a multivalent anion, or with multiple monovalent anions. The complexes may be administered orally to a patient as a cholinergic agent, or for some other purpose. Numerous modifications are contemplated, including modifications to the ring structure of the compound, and substitution and functionalization of the ring. Other contemplated modifications include the use of different anions, including various monovalent and polyvalent anions, and both organic and inorganic anions.

DETAILED DESCRIPTION

As used herein, the term "quaternary ammonium cholinergic agents" is used generically to mean Pyridostigmine, Neostigmine, Edrophonium, and substituted or functionalized analogues of these compounds. Accordingly, multivalent salts of any of these compounds are sometimes referred to herein as multivalent quaternary ammonium cholinergic agent salts. Other chemical terms have their normally accepted meanings.

Figure 1:
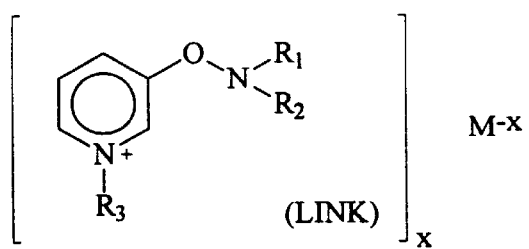
FIG. 1 is a generalized formula for a class of polyvalent quaternary ammonium cholinergic agent salts according to one aspect of the present invention.
Figure 2:
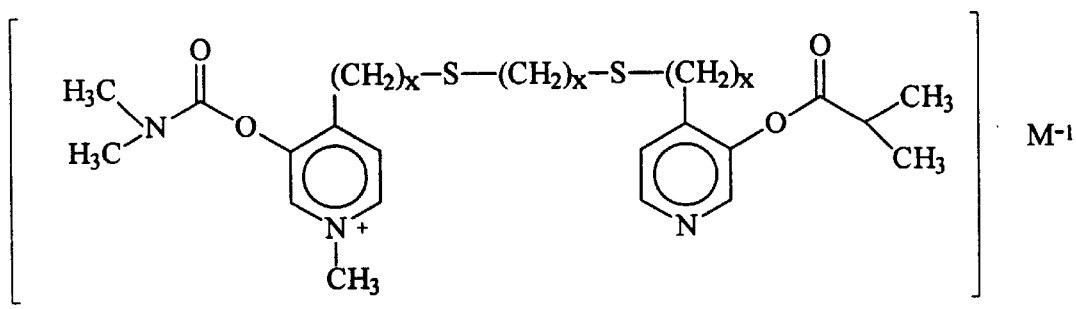
FIG. 2 is a generalized formula for a second class of polyvalent quaternary ammnonium cholinergic agent salts according to another aspect of the present invention.
Figure 3:
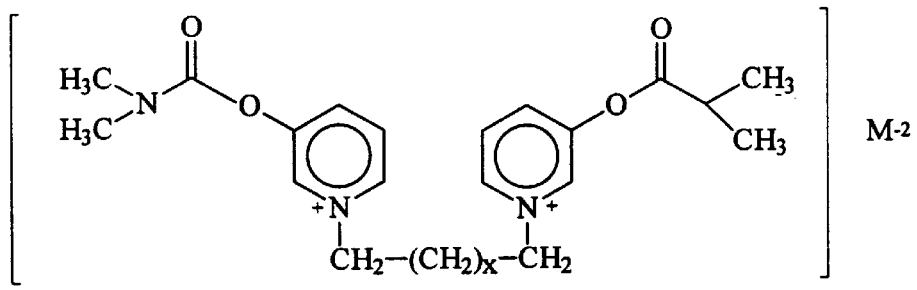
FIG. 3 is a generalized formula for a third class of polyvalent quaternary ammonium cholinergic agent salts according to another aspect of the present invention.
Figure 4:
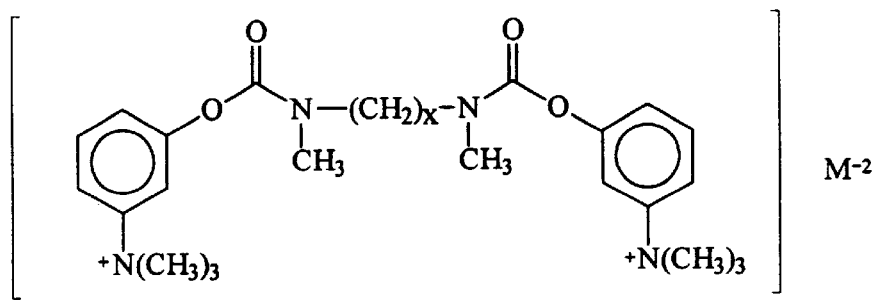
FIG. 4 is a generalized formula for a fourth class of polyvalent quaternary ammonium cholinergic agent salts according to another aspect of the present invention.
Figure 5:
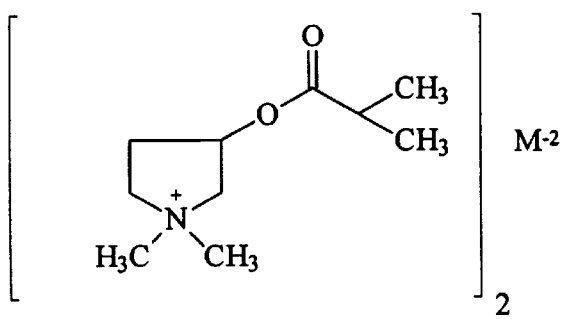
FIG. 5 is a generalized formula for a fifth class of polyvalent quaternary ammonium cholinergic agent salts according to another aspect of the present invention.
Figure 6:
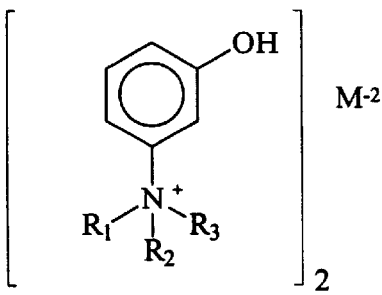
FIG. 6 is a generalized formula for a sixth class of polyvalent quaternary ammonium cholinergic agent salts according to another aspect of the present invention.
Figure 7:
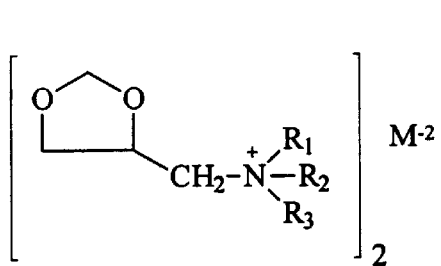
FIG. 7 is a generalized formula for a seventh class of polyvalent quaternary ammonium cholinergic agent salts according to another aspect of the present invention.
Figure 8:
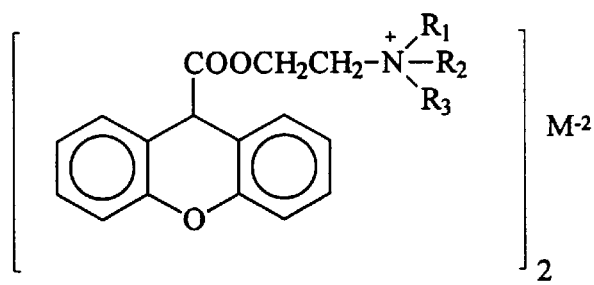
FIG. 8 is a generalized formula for a eighth class of polyvalent quaternary ammonium cholinergic agent salts according to another aspect of the present invention.
Figure 9:
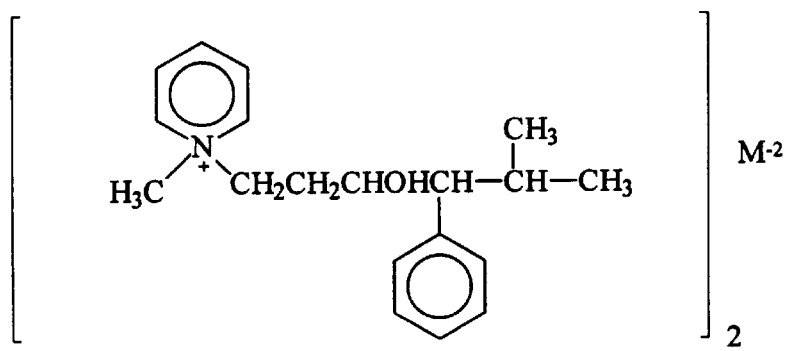
FIG. 9 is a generalized formula for a ninth class of polyvalent quaternary ammonium cholinergic agent salts according to another aspect of the present invention.
Figure 10:
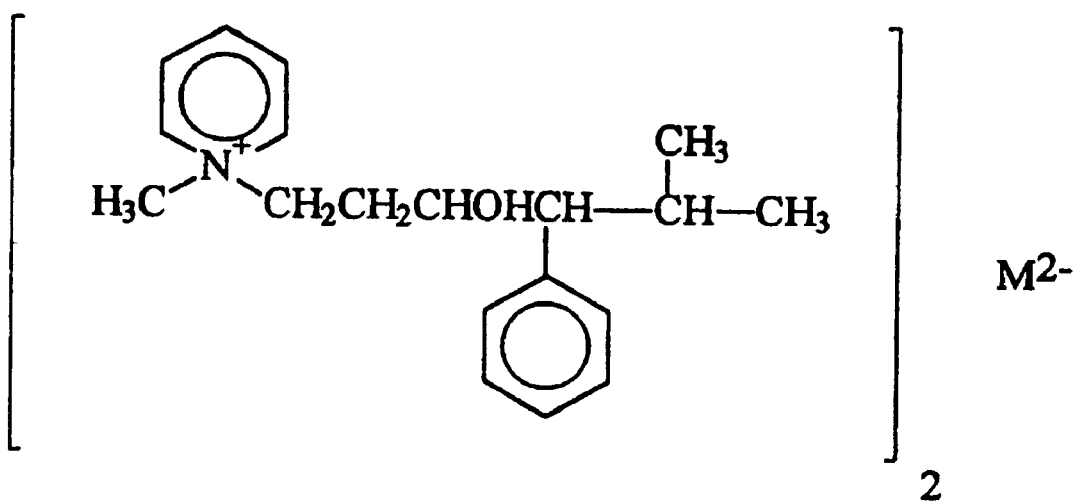

There are numerous compounds contemplated herein, several examples of which are depicted in the FIGS. 1–10. These compounds all have the following structure:

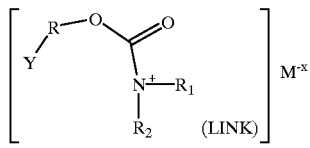

wherein;
M is a monovalent anion, a plurality of monovalent anions, or a polyvalent anion;
R is a ring or ring system;
Y is alkyl, substituted alkyl, aryl, substituted aryl, aralkyl, substituted aralkyl, or $NR_3R_4R_5$
  where $R_1$, $R_2$, $R_3$, $R_3$, $R_4$ and $R_5$ are independently H, alkyl, substituted alkyl, aryl, or substituted aryl;
x is an integer greater than 1; and
(LINK) is an optional linker.

The ring or ring system is contemplated to include at least one five or six member ring, which may be unsubstituted carbon, or may be a heterocycle having one or more sulphur, nitrogen or other substitutions. The ring(s) may be aromatic or non-aromatic. Preferred rings include pyridine, pyrimidine, aza pyrimidine and benzene.

Preferred an ions includ e inorganic and organic ions, and specifically include tribromide $(Br_3)^{-3}$, carbonate $CO_3^{-2}$, nitrate $NO_2^{-2}$, sulfate $SO_4^{-2}$, hydrogen phosphate $HPO_4^{-2}$, phosphite $PO_3^{-2}$, phosphate $PO_4^{-3}$, and an organic acid anions including dicarboxylic anions such as the anions of oxalic, malonic, succinic and phthalic acids. Where a plurality of monovalent anions are employed, it is contemplated that the anions may comprise halogens, $HCO_3^-$, $CH_3COO^-$, $CH_3SO_4^-$, $CH_3SO_3^-$ and $C_4H_5O_6^-$.

Preferred linkers include an aliphatic chain of one to ten atoms. The backbone of the chain may or may not be entirely comprised of carbon, and may or may not be substituted or branched. Most preferred (LINK), however, will be —S— or —$(CH_2)_n$— where n is an integer from 1 to 4. (LINK) typically does not couple the underlying molecules directly at the ring members, but through functionalities extending from the rings.

FIGS. 1–9 depict nine different classes of compounds which are contemplated herein. The structures are deemed to be self explanatory.

Synthesis

The synthesis of multivalent quaternary ammonium cholinergic agent salts is straightforward. In one method, a monovalent salt of an active moiety (such as pyridostigmine bromide) is run through an cation exchange column. A suitable resin for this purpose is Amberlite. This produces the following reactions:

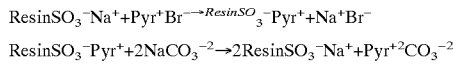

$$ResinSO_3^-Na^+ + Pyr^+Br^- \xrightarrow{ResinSO_3} Pyr^+ + Na^+Br^-$$

$$ResinSO_3^-Pyr^+ + 2NaCO_3^{-2} \rightarrow 2ResinSO_3^-Na^+ + Pyr^{+2}CO_3^{-2}$$

The process uses approximately 23 meq of resin for 3 g Pyridostigmine bromide, and 23 meq ≈ 12 ml resin bed. A more detailed procedure is as follows: (1) Prepare 12 ml resin bed Amberlite IR-116 (NA+form) in 25 ml plastic pipette with glass wool plug. (2) Rinse column with deionized water until clear. (3) Weigh out 6 g pyridostigmine bromide. Dissolve in 10 ml of deionized water. Final volume approx. 13.5 ml. (4) Pipette 6.7 ml (3 g) of Pyridostigmine bromide solution onto resin bed. (5) Drain solution through the column (bed does not go dry). (6) Rinse column with approx. 30 ml deionized water until collected drops no longer show precipitate with $AgNO_3$ solution. Pipette 4 ml (10 meq.) of $Na_2CO_3$ solution onto resin bed, and rinse through with 20 ml deionized water. Collect in 250 ml flask. (8) Evaporate solution in flask to dryness on a vacuum rotary evaporator. (9) Collect solid material onto glass storage vial. Test Results Pyridostigmine carbonate was synthesized as described above. When placed in HCl, the product dissociates into the corresponding pyridostigmine, which was verified by absorption spectra at 269 nm Pharmaceutical Formulations As with other pharmaceutical formulations, multivalent quaternary ammonium cholinergic salts may be adapted for administration to the body in a number of ways suitable for the selected method of administration, including orally, intravenously, intramuscularly, intraperitoneally, topically, and the like. In addition to comprising one or more different multivalent quaternary ammonium cholinergic agent salts, the subject pharmaceutical formulations may comprise one or more non-biologically active compounds, i.e., excipients, such as stabilizers (to promote long term storage), emulsifiers, binding agents, thickening agents, salts, preservatives, and the like.

Multivalent quaternary ammonium cholinergic salts can be employed in dosages and amounts which are conventional in the art for the underlying quaternary ammonium cholinergic agent or quaternary ammonium cholinergic agent like compound, but adjusted for more efficient absorption, transport and cellular uptake. Thus, for pyridostigmine, which can be given orally at 1–3 180 mg tablets once or twice daily, the dosage of the corresponding multivalent quaternary ammonium cholinergic agent salt may still be 1–3 180 mg tablets once or twice daily. The daily dosage may be administered all at once, or may be divided into a number of smaller doses which are then administered at intervals of time.

The dosage regimen may be adapted to provide the optimum therapeutic response. For example, the most preferred dosage will vary with the particular agent chosen, and during the course of administration the dose may be proportionally increased or reduced as indicated by the exigencies of the therapeutic situation.

Multivalent quaternary ammonium cholinergic agent salts may be administered in any convenient manner, such as by oral, intravenous, intraperitoneal, intramuscular, or subcutaneous or other known routes. For oral administration, multivalent quaternary ammonium cholinergic agent salts may be administered with an inert diluent or with an assimilable edible carrier, or multivalent quaternary ammonium cholinergic agent salts may be incorporated directly with the food of the diet. Orally administered multivalent quaternary ammonium cholinergic agent salts may be incorporated with excipients and used in the form of ingestible tablets, buccal tablets, troches, capsules, elixirs, suspension syrups, wafers, and the like.

The tablets, troches, pills, capsules and the like may also contain the following: a binder, such as gum tragacanth, acacia, cornstarch, or gelatin; excipients, such as dicalcium phosphate; a disintegrating agent such as corn starch, potato starch, alginic acid and the like; a lubricant such as magnesium stearate; and a sweetening agents, such as sucrose, lactose or saccharin; a flavoring agent such as peppermint, oil of wintergreen, or cherry flavoring. When the dosage unit is a capsule, it may contain, in addition to materials of the above type, a liquid carrier. Various other materials may also be present as coatings or to otherwise modify the physical form of the dosage unit. For instance, tablets, pills, or capsules may be coated with shellac, sugar or both. A syrup or elixir may contain sucrose as a sweetening agent, methyl and propylparabens as preservatives, a dye and flavoring such as cherry or orange flavor. Such additional materials should be substantially non-toxic in the amounts employed. Furthermore, the multivalent quaternary ammonium cholinergic agent salts may be incorporated into sustained-release preparations and formulations.

Formulations for parenteral administration may include sterile aqueous solutions or dispersions, and sterile powders for the extemporaneous preparation of sterile, injectable solutions or dispersions. The solutions or dispersions may also contain buffers, diluents, and other suitable additives, and may be designed to promote the cellular uptake of the multivalent quaternary ammonium cholinergic agent salts in the composition, e.g., the multivalent quaternary ammonium cholinergic agent salts may be encapsulated in suitable liposomes. Preferably the solutions and dispersions for parenteral administration are sterile and sufficiently fluid for proper administration, sufficiently stable for manufacture and use, and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by maintenance of the required particle size in the case of dispersion and by the use of surfactants.

Sterile injectable solutions are prepared by incorporating the active compounds in the required amount in the appropriate solvent with one or more of the various other ingredients described above, followed by sterilization. Dispersions may generally be prepared by incorporating the various sterilized active ingredients into a sterile vehicle which contains the basic dispersion medium and the required other ingredients from those listed above. In the case of sterile powders used to prepare sterile injectable solutions, the preferred methods of preparation are vacuum-drying and freeze-drying techniques which yield a powder of the active ingredient plus any additional desired ingredient from previously sterile-filtered solutions.

Pharmaceutical formulations for topical administration may be especially useful with certain bio-active compounds for localized treatment. Formulations for topical treatment included ointments, sprays, gels, suspensions, lotions, creams, and the like. Formulations for topical administration may include, in addition to the subject multivalent quaternary ammonium cholinergic agent salts, known carrier materials such as isopropanol, glycerol, paraffin, stearyl alcohol, polyethylene glycol, etc. The pharmaceutically acceptable carrier may also include a known chemical absorption promoter. Examples of absorption promoters are e.g., dimethylacetamide (U.S. Pat. No. 3,472,931), trichloroethanol or trifluoroethanol (U.S. Pat. No. 3,891,757), certain alcohols and mixtures thereof (British Patent No. 1,001,949), and British patent specification No. 1,464,975.

Solutions of the multivalent quaternary ammonium cholinergic agent salts may be prepared in water suitably mixed with a surfactant such as hydroxypropylcellulose. Dispersions can also be prepared in glycerol, liquid polyethylene glycols, and mixtures thereof and in oils. These compositions and preparations may advantageously contain a preservative to prevent the growth of microorganisms.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents such as sodium chloride. Prolonged delivery of injectable compositions can be brought about by the use of agents which delay absorption, such as aluminum monostearate and gelatin.

The compositions and preparations described preferably contain at least 0.1% of active multivalent quaternary ammonium cholinergic agent salt. The percentage of the compositions and preparations may, of course, be varied, and may contain between about 2% and 60% of the weight of the amount administered. The amount of active compounds in such therapeutically useful compositions and preparations is such that a suitable dosage will be obtained.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the therapeutic active ingredients, its use in the therapeutic compositions and preparations is contemplated. Supplementary active ingredients can also be incorporated into the compositions and preparations.

The terms "treatment" or "treating" as used herein with reference to a disease refers both to prophylaxis and to the amelioration of symptoms already present in an individual. It will be appreciated by the person of ordinary skill in the art that a treatment need not be completely effective in preventing the onset of a disease or in reducing the symptoms associated with the disease. Any perceived reduction of the severity of symptoms, delay in the onset of symptoms, or delay in the progression of severity of symptoms is desirable to a patient. In addition to the therapeutic uses of the subject multivalent quaternary ammonium cholinergic agent salts, the multivalent quaternary ammonium cholinergic agent salts may also be used as a laboratory tool for the study of absorption, distribution, cellular uptake, and efficacy.

Equivalents

The foregoing written specification is considered to be sufficient to enable one skilled in the art to practice the invention. Indeed, various modifications of the above-described makes for carrying out the invention which are obvious to those skilled in the field of organic chemistry or related fields are intended to be within the scope of the following claims.

We claim:

1. A pharmaceutically effective cholinergic compound having a plurality of carbamate chemical groupings according to the formula, $[Y—R—O—CO—NR_1R_2]^+$, the groupings covalently bound together in any of the following ways:

(a) through the nitrogen atom alpha to the carbamate carbonyl; and (b) through a quaternary nitrogen atom in the ring structure of R;

wherein R is a ring or ring system, Y is alkyl, substituted alkyl, aryl, substituted aryl, aralkyl, substituted aralkyl, or $NR_3R_4R_5$ where $R_1$, $R_2$, $R_3$, $R_3$, $R_4$ and $R_5$ are independently H, alkyl, substituted alkyl, aryl, or substituted aryl;

wherein all atoms external to and which covalently link two Rs have a neutral charge.

2. The compound of claim 1 wherein R is a six member heterocycle.

3. The compound of claim 1 wherein R is a six member heterocycle and Y is covalently bonded to R at a Nitrogen.

4. The compound of claim 1 wherein R is pyrimidine.

5. The compound of claim 1 wherein R is aza pyrimidine.

6. The compound of claim 1 wherein R is phenyl and Y is $NR_3R_4R_5$.

7. The compound of claim 1 wherein R is a five member heterocycle.

8. The compound of claim 1 further containing tribromide.

9. The compound of claim 1 further containing an anion selected from the group consisting of carbonate, nitrate, and sulfate.

10. The compound of claim 1 further containing an anion selected from the group consisting of hydrogen phosphate, phosphite, and phosphate.

11. The compound of claim 1 further containing an organic acid anion.

12. The compound of claim 1 further containing an anion selected from the group consisting of carbonate, nitrate, sulfate, hydrogen phosphate, phosphite, phosphate, and an organic acid anion.

13. The compound of claim 1 wherein the groupings are covalently bound through an aliphatic chain of one to ten atoms.

14. The compound of claim 1 wherein the groupings are covalently bound through an aliphatic chain of one to ten atoms, and further containing an anion selected from the group consisting of carbonate, nitrate, sulfate, hydrogen phosphate, phosphite, phosphate, and an organic acid anion.

15. A method of treating a condition responsive to a cholinergic agent comprising administering to a patient an effective amount of the compound of claim 1.

16. A method of treating mysasthenia gravis comprising administering to a patient an effective amount of the compound of claim 1.

17. A method of treating carpal tunnel syndrome comprising administering to a patient an effective amount of the compound of claim 1.

18. The compound according to claim 1 which dissociates under physiologic conditions to produce Pyridostigmine.

19. The compound according to claim 1 which dissociates under physiologic conditions to produce Neostigmine.

20. The compound according to claim 1 which dissociates under physiologic conditions to produce Edrophonium.

* * * * *